US006444452B1

(12) United States Patent
Keri et al.

(10) Patent No.: US 6,444,452 B1
(45) Date of Patent: Sep. 3, 2002

(54) PROCESS FOR RECOVERING STATIN COMPOUNDS FROM A FERMENTATION BROTH

(75) Inventors: Vilmos Keri; Lajos Deak; Ilona Forgacs; Csaba Szabo; Edit Arvai Nagyne, all of Debrecen (HU)

(73) Assignee: Biogal Gyogyszergyar Rt., Debrecen (HU)

( * ) Notice: Subject to any disclaimer, the term of this patent is extended or adjusted under 35 U.S.C. 154(b) by 0 days.

(21) Appl. No.: 09/723,711

(22) Filed: Nov. 28, 2000

Related U.S. Application Data

(60) Provisional application No. 60/168,056, filed on Nov. 30, 1999.

(51) Int. Cl.$^7$ .................. C12P 7/62; C07D 239/72; C07D 309/30; C07C 69/74; C07C 69/66
(52) U.S. Cl. .................. 435/135; 435/41; 425/305; 453/125; 453/135; 453/252.1; 453/253.5; 544/292; 549/292; 560/119; 560/188; 560/256
(58) Field of Search .................. 435/135, 41; 425/305; 453/125, 135, 252.1, 253.5; 544/292; 549/292; 560/119, 188, 256

(56) References Cited

U.S. PATENT DOCUMENTS

| 4,346,227 | A |   | 8/1982 | Terahara et al. |
| 5,153,124 | A | * | 10/1992 | Furuya et al. ............... 435/125 |
| 5,202,029 | A |   | 4/1993 | Haytko et al. |
| 5,616,595 | A |   | 4/1997 | Chu et al. |
| 5,712,130 | A |   | 1/1998 | Hajko et al. |
| 5,942,423 | A |   | 8/1999 | Demain et al. |

FOREIGN PATENT DOCUMENTS

| WO | WO/98/37220 | * | 8/1998 |
| WO | WO 99/10499 |   | 3/1999 |
| WO | WO 00146175 |   | 8/2000 |
| WO | WO 01/03647 A2 |  | 1/2001 |

OTHER PUBLICATIONS

Budavari, et al. The Merck Index. 1989. Merck and Co., Inc., p., 1222.*

T. Koga et al., "Tissue–selective inhibition of cholesterol synthesis in vivo by pravastatin sodium, a 3–hydroxy–3–methylglutaryl coenzyme A reductase inhibitor", *Biochimica et Biophysica Acta*, vol. 1045, No. 1, pp. 115–120, Jun. 28, 1990.

Serajuddin et al. "Relative Lipophilicities, Solubilities, and Structure–Pharmacological Considerations of 3–Hydroxy–3–Methylglutaryl–Coenzyme A (HMG–CoA) Reductase Inhibitors Pravastatin, Lovastatin, Mevastatin, and Simvastatin", *Journal of Pharmaceutical Sciences*, vol. 80, No. 9, pp. 830–834, Sep. 1991.

\* cited by examiner

*Primary Examiner*—Christopher R. Tate
*Assistant Examiner*—Kailash C. Srivastava
(74) *Attorney, Agent, or Firm*—Kenyon & Kenyon

(57) ABSTRACT

A novel process for recovering a compound from a fermentation broth that includes the stages of forming an enriched solution of the compound by extraction, obtaining a salt of the compound from the enriched solution, purifying a salt of the compound and trans-salifying the salt of the compound to a metal salt of the compound is disclosed.

44 Claims, No Drawings

PROCESS FOR RECOVERING STATIN COMPOUNDS FROM A FERMENTATION BROTH

RELATED APPLICATION

This application claims the benefit under 35 U.S.C. §119(e) of U.S. Provisional Patent Application No. 60/168,056, filed Nov. 30, 1999.

FIELD OF THE INVENTION

The present invention relates to methods for isolating desired chemical products of reactions conducted in aqueous fermentation broths. The invention further relates to isolation of pravastatin, compactin and lovastatin from a fermentation broth and in particular to isolation of pravastatin made by fermentation of compactin.

BACKGROUND OF THE INVENTION

Complications of cardiovascular disease, such as myocardial infarction, stroke, and peripheral vascular disease account for half of the deaths in the United States. A high level of low density lipoprotein (LDL) in the bloodstream has been linked to the formation of coronary lesions which obstruct the flow of blood and can rupture and promote thrombosis. Goodman and Gilman, *The Pharmacological Basis of Therapeutics* 879 (9th ed. 1996). Reducing plasma LDL levels has been shown to reduce the risk of clinical events in patients with cardiovascular disease and in patients who are free of cardiovascular disease but who have hypercholesterolemia. Scandinavian Simvastatin Survival Study Group, 1994; Lipid Research Clinics Program, 1984a, 1984b.

Statin drugs are currently the most therapeutically effective drugs available for reducing the level of LDL in the blood stream of a patient at risk for cardiovascular disease. This class of drugs includes, inter alia, compactin, lovastatin, simvastatin, pravastatin and fluvastatin. The mechanism of action of statin drugs has been elucidated in some detail. They disrupt the synthesis of cholesterol and other sterols in the liver by competitively inhibiting the 3-hydroxy-3-methyl-glutaryl-coenzyme A reductase enzyme ("HMG-CoA reductase"). HMG-CoA reductase catalyzes the conversion of HMG-CoA to mevalonate, which is the rate determining step in the biosynthesis of cholesterol. Consequently, its inhibition leads to a reduction in the rate of formation of cholesterol in the liver.

Pravastatin is the common medicinal name of the chemical compound [1S-[1α(β*,δ*)2α, 6α,8β(R*),8aα]]-1,2,6,7,8,8a-hexahydro-β,δ,6-trihydroxy-2-methyl-8-(2-methyl-1-oxobutoxy)-1-naphthalene-heptanoic acid. (CAS Registry No. 81093-370.) The molecular structure of pravastatin in free acid form is represented by Formula (Ia) where R═OH. The lactone form is represented by Formula (Ib), with atoms labeled to indicate numbering of the atoms.

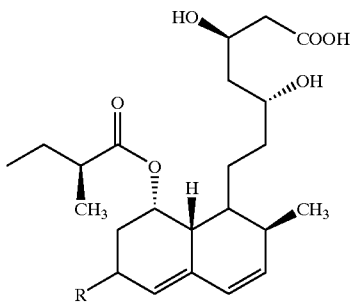

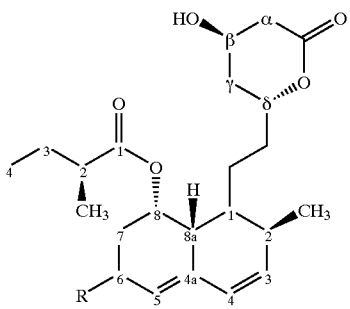

Pravastatin, compactin (Formula Ib, R═H), lovastatin (Formula Ib, R═CH$_3$), simvastatin, and fluvastatin each possess an alkyl chain that is terminated by a carboxylic acid group closed in a lactone and that bears two hydroxyl groups at the β and δ positions with respect to the carboxylic acid group. This alkyl chain is the portion of the molecule that binds to HMG-CoA reductase. The carboxylic acid group and the hydroxyl group at the δ position are prone to lactonize as shown in formula (Ib). Lactonizable compounds like the statins may exist in the free acid form or the lactone form or as an equilibrium mixture of both forms. Lactonization causes processing difficulties in the manufacture of statin drugs because the free acid and the lactone forms of the compounds have different polarities. A method of purifying one form is likely to remove the other form along with the impurities resulting in a lower yield. Consequently, great care must ordinarily be exercised when handling lactonizable compounds in order to isolate them in high yield.

Pravastatin exhibits an important therapeutic advantage over other statins. Pravastatin selectively inhibits cholesterol synthesis in the liver and small intestine but leaves cholesterol synthesis in the peripheral cells substantially unaffected. Koga, T. et al. *Biochim. Biophys. Acta*, 1990, 1045, 115–120. This selectivity appears to be due, in part, to the presence of a hydroxyl group at the C-6 position of the hexahydronaphthalene nucleus. The C-6 position is occupied by a hydrogen atom in compactin and a methyl group in lovastatin. Pravastatin is less able to permeate the lipophilic membranes of peripheral cells than the other more lipophilic congeners, Serajuddin et al., *J Pharm. Sci.*, 1991, 80, 830–34, and the limited mobility of pravastatin is thought to account for its more localized action in the liver and intestine.

According to U.S. Pat. No. 4,346,227, incorporated herein by reference, pravastatin is reported as having been first isolated as a metabolite of compactin by M. Tanaka et al. during a study of compactin metabolism. According to the '227 patent, pravastatin can be obtained by fermentation of compactin using a variety of microorganisms: *Absidia coerulea* IFO 4423 spores, *Cunninghamella echinulata* IFO 4445, *Streptomyces rosochromogenus* NRRL 1233, *Syncephalastrum racemosum* IFO 4814 and *Syncephalastrum racemosum* IFO 4828. After fermentation, pravastatin was separated from the fermentation broth by acidifying the broth to a pH of 3 and extracting pravastatin and other non-hydrophilic organics with ethyl acetate, followed by washing with brine. The pravastatin free acid was lactonized by addition of a catalytic amount of trifluoroacetic acid, then neutralized with dilute sodium bicarbonate, dried over sodium sulfate and evaporated to dryness. The residue was purified by preparative reverse-phase high performance liquid chromatography ("HPLC"). One skilled in the art will appreciate that reverse-phase HPLC is not an economical method of purification for large-scale preparation of a chemical compound.

U.S. Pat. No. 5,942,423 relates to the microbial hydroxylation of compactin to pravastatin using a strain of Actinomadura. The only isolation method presented in the examples is the isolation of minute quantities attendant to analytical scale HPLC analysis of the fermentation broth. According to a more general discussion about isolating pravastatin from the broth, the preferred method of isolation is HPLC.

Commonly-assigned, co-pending PCT Application Serial No. PCT/US00/19384 relates to the microbial hydroxylation of compactin to pravastatin using a strain of *Micromonospora maculata* that is unusually resistant to the antifungal effects of compactin.

U.S. Pat. No. 5,202,029 relates to a process of purifying HMG-CoA reductase inhibitors using HPLC. Following separation of the impurities on the HPLC column, the HMG-CoA reductase inhibitor elutes from the HPLC column as a solute dissolved in the eluent. The eluent is partially evaporated and then water is added to induce crystallization of the HMG-CoA reductase inhibitor.

U.S. Pat. No. 5,616,595 relates to a continuous process for recovering water-insoluble compounds from a fermentation broth by tangential filtration. The fermentation broth is cycled past a filter. The broth becomes increasingly concentrated with each cycle because of loss of water through the filter. Once a desired concentration is reached, the concentrated broth is then slurried with a solvent in which the desired compound is soluble. The slurry is then cycled past the filter. The solution of the desired compound is collected as the filtrate and the desired compound is then isolated from the filtrate and optionally subjected to further purification. The method is said to be applicable to a wide variety of compounds including lovastatin, pravastatin and simvastatin.

A process for isolating lovastatin in the lactone form is described in U.S. Pat. No. 5,712,130. In this process, lovastatin is extracted from a fermentation broth with butyl acetate. The resulting solution is then centrifuged and an aqueous phase that separates out is discarded. The organic phase is vacuum distilled at above 40° C., which, in addition to concentrating the solution, promotes lactonization by removal of water. Crystals of lovastatin lactone crystallize upon cooling and are recrystallized to a purity of 90% or greater. Those of skill in the art will appreciate that this method is ill-suited to isolation of the free carboxylic acid or a carboxylate salt form of a statin.

Presently, the most economically feasible method of making pravastatin is by enzymatic hydroxylation of compactin at the C-6 position. However, the known methods of isolating a statin from a fermentation broth are ill-suited for isolating pravastatin as its sodium salt, do not achieve a pharmaceutically acceptable level of purity, or require chromatographic separation to achieve high purity. The present invention meets a need in the art for an efficient method of isolating pravastatin from a fermentation broth in high purity, in high yield, on a preparative scale and without the need for chromatographic purification.

SUMMARY OF THE INVENTION

It is an object of the present invention to provide an efficient method of isolating a statin compound from an aqueous fermentation broth. In particular, the present invention provides an industrial preparative scale method for purifying pravastatin, compactin and lovastatin without a need for chromatographic separation.

It is a further object of the invention to obtain pravastatin in a highly pure form and in high yield so that the remarkable stereoselectivity and regioselectivity of microbial transformations may attain, as well, a higher yield and greater economy. The pravastatin is separated from the broth with a minimum consumption of solvent, purified in high yield, and transformed to its pharmaceutically acceptable sodium salt.

The process involves extraction of pravastatin from an aqueous fermentation broth into an organic solvent, back-extraction of pravastatin into a basic aqueous solution and, optionally, a re-extraction into an organic solvent or concentration of the aqueous solution, resulting in either an aqueous or organic solution that is enriched in pravastatin relative to the initial concentration of pravastatin in the fermentation broth. The pravastatin is obtained from the enriched solution by precipitation of its metal or ammonium salt and then purified by recrystallization of the pravastatin salt. The recrystallized salt is then trans-salified to form pravastatin sodium salt and any excess sodium ions are scavenged with an ion exchange resin. The sodium salt of pravastatin may then be isolated from solution by recrystallization, lyophilization or other means.

DETAILED DESCRIPTION OF THE INVENTION

The present invention is a process for isolating pravastatin, compactin and lovastatin from an aqueous fermentation broth. The invention is illustrated by isolation of pravastatin sodium from a fermentation broth. However, it will be understood that the process can be used to purify other compounds made by a microbial or an enzymatic process.

Enzymatic Hydroxylation of Compactin

Pravastatin sodium is synthesized by enzymatic hydroxylation of compactin such as described in U.S. Pat. Nos. 5,942,423 and 4,346,227. The hydroxylation broth from which pravastatin is to be isolated can be any of the aqueous broths known for industrial scale fermentation of compactin. If the broth is neutral or basic upon completion of the fermentation, then an acid is added to it to bring the broth to a pH of between about 1 and 6, preferably between 1 and 5.5 and more preferably between 2 and 4. Acids that may be used include hydrochloric acid, sulfuric acid, trifluoroacetic acid or any other protic acid, preferably one having a pH of less than 1 as a 1M solution in water. Acidification of the fermentation broth converts any pravastatin carboxylate salts in the broth to the free acid and/or lactone.

Isolation of Pravastatin Sodium

The process of the present invention involves the steps of forming an enriched solution of pravastatin, obtaining a salt of pravastatin from the enriched solution, purifying the pravastatin salt, trans-salifying the pravastatin salt to the pravastatin sodium salt and isolating the pravastatin sodium salt.

In the first step, pravastatin is obtained from an aqueous fermentation broth at a relatively highly concentrated solution by a sequence of extraction, back-extraction operations. Fermentation is typically conducted at very high dilution. Through dilution, the broth attains a higher maximum enzyme potential. A disadvantage of high dilution is that a large volume of fermentation media must be manipulated until the desired product is obtained in a more enriched form. The large volume also places stringent requirements upon the method of isolation. Chromatographic methods are generally impractical for separation of such large volumes, particularly where the solvent is water. If the isolation is conducted by extraction, the organic extraction solvent must have sufficient polarity to compete with water for favorable partitioning of the product yet not be so polar as to be substantially soluble in water. If the extraction is inefficient, large volumes of organic solvent are required to isolate the desired product in high yield, with attendant risks to the health and safety of personnel in and around the fermentation facility.

We have found that $C_2$–$C_4$ alkyl formates and $C_1$–$C_4$ alkyl esters of $C_2$–$C_4$ carboxylic acids are capable of highly efficient extraction of pravastatin from an aqueous fermentation broth. The partition coefficient of the pravastatin lactone typically is 1000:1 or higher and the partition coefficient of the free acid typically is 10:1 or higher. The alkyl group may be linear, branched or cyclic. Preferred esters include ethyl formate, n-propyl formate, i-propyl formate, n-butyl formate, s-butyl formate, i-butyl formate, t-butyl formate, methyl acetate, ethyl acetate, n-propyl acetate, i-propyl acetate, n-butyl acetate, s-butyl acetate, i-butyl acetate, t-butyl acetate, methyl propionate, ethyl propionate, n-propyl propionate, i-propyl propionate, butyl propionate, methyl butyrate, ethyl butyrate, n-propyl butyrate, i-propyl butyrate, butyl butyrates, methyl isobutyrate, ethyl isobutyrate, propyl isobutyrates and butyl isobutyrates. Of these preferred organic solvents we have found that ethyl acetate, i-butyl acetate, propyl acetate and ethyl formate are especially well suited. The most preferred extraction solvent is i-butyl acetate. Other organic solvents may be substituted for the esters. Halogenated halocarbons, aromatic compounds, ketones and ethers may be used, such as dichloromethane, chloroform, carbon tetrachloride, 1,2-dichloroethane, benzene, butyl methyl ketone, diethyl ether and methyl t-butyl ether.

In the enrichment step of our invention, an organic extract is formed by contacting an organic extraction solvent, preferably selected from the list above, with the fermentation broth. The pH of the fermentation broth is between about pH 1 to about pH 6. Preferably, the pH is between about pH 2 to about pH 4.

Any equipment adapted for mixing large volumes of liquid in either a batch or continuous process may be used. Since fermentation is typically conducted as a batch process, a batchwise isolation process is a natural choice. Accordingly, conventional high volume mixers and settling tanks or equipment adapted for both mixing and phase separation may be used. In the preferred mode of this aspect of the invention a minor portion, preferably less than 50% (v/v), of the extraction solvent is contacted with the fermentation broth, preferably with mild mechanical agitation. After contacting and phase separation, the extraction solvent containing pravastatin is separated from the pravastatin-depleted fermentation broth. The broth may then be contacted with organic extraction solvent one or more times and each of the resulting organic extracts may be combined. The volume of the resulting organic extract of pravastatin may be either greater or less than the volume of the fermentation broth.

The second operation toward forming an enriched solution of pravastatin is back-extraction of the pravastatin into a basic aqueous solution. Back-extraction removes some or all non-polar organic impurities and, if pravastatin lactone is present, promotes reopening of the pravastatin lactone ring. Although not intending to be limited in any way by a particular chemical theory or mechanism, according to well-established chemical theory pravastatin is in carboxylate anion form in the basic aqueous extract. Back-extraction may be used to concentrate the pravastatin by using a volume of aqueous base that is less than the volume of the organic extract. The base is preferably NaOH, $NH_4OH$ or KOH, most preferably $NH_4OH$ or NaOH, and the basic aqueous solution preferably has a pH of between about 7.0 and about 13.7, more preferably between about 7 and about 13, most preferably between about 7.5 and about 11. The extraction solvent is contacted with the basic aqueous solution until the amount of pravastatin in the organic phase has been substantially depleted as determined by thin layer chromatography or any other method including the subjective judgment that sufficient contacting has occurred for complete extraction. Multiple back-extractions may be performed for optimal recovery. However, a single back-extraction is highly efficient when the organic phase is butyl acetate. Preferably, the back-extraction is conducted with a volume of basic aqueous solution that is less than one third of the volume of the organic extract, more preferably less than one fourth and most preferably, about one fifth of the volume of the organic extract. The preferred concentration range of the enriched aqueous solution from which pravastatin is obtained later in the process is from about 2 to about 50 g/L, more preferably from about 5 to about 15 g/L.

The aqueous extract may be further concentrated by distillation, preferably vacuum distillation, to increase the concentration of the solution. Before further concentrating the aqueous extract by distillation the pH should be adjusted between about pH 7 to about pH 13.7, preferably to between about pH 7.5 and about pH 11 and more preferably to between about pH 8 and about pH 10. Vacuum distillation may be done by heating the aqueous extract from about 30° C. to about 80° C. under 5–120 mm Hg absolute pressure. The choice of other vacuum distillation conditions is well within the capabilities of those skilled in arts to which this process relates.

As an alternative to obtaining pravastatin from an enriched aqueous solution later in the process, pravastatin may be obtained from an enriched organic solution. The enriched organic solution of pravastatin is formed by re-extracting the pravastatin into an organic solvent after the aqueous extract has been reacidified with an acid, preferably trifluoroacetic acid, hydrochloric acid, sulfuric acid, acetic acid, or phosphoric acid, more preferably sulfuric or phosphoric acid, to a pH of about 1.0 to about 6.5, more preferably about 2.0 to about 4.0. Depending upon conditions, the pravastatin carboxylate anion may be protonated to the pravastatin free acid, which is less polar than the carboxylate or lactonized to a yet less polar form.

Pravastatin is re-extracted into a re-extraction solvent selected from the organic solvents previously described as suitable for extracting pravastatin from the fermentation broth. The organic solvent may be, but need not be, the same solvent used to extract pravastatin from the fermentation broth. In this re-extraction, further enrichment of pravastatin is accomplished by re-extracting into an amount of organic solvent that is preferably less than about 50% (v/v) of the aqueous extract, more preferably from about 33% (v/v) to about 20% (v/v) and still more preferably about 25% (v/v)

the volume of the aqueous extract. Accordingly, as further exemplified in Example 1, pravastatin may be concentrated from 100 L of fermentation broth to 8 L of enriched organic solution in 89% yield from the initial organic extract. It will be appreciated by those skilled in the art that a higher yield of purified pravastatin may be attained by performing multiple extractions where only a single extraction has been described in this preferred mode for practicing the invention. This preferred mode achieves a balance of solvent economy and high product yield. Deviations from this preferred mode which further enhance the yield by repeated extractions where only one has been described above do not necessarily depart from the spirit of the invention. Before proceeding to obtain pravastatin from the enriched organic solution by "salting out," the enriched organic solution is preferably dried, which may be done using a conventional drying agent such as $MgSO_4$, $Na_2SO_4$, $CaSO_4$, silica, perlite and the like, and optionally decolorized with activated carbon. A dried and/or decolorized enriched organic solution is then separated conventionally, as for instance by filtration or decanting.

In the next step of our process, a salt of pravastatin is obtained from the enriched aqueous or organic solution, as the case may be. The salt is obtained by precipitation from the enriched solution. Precipitation is induced by adding to the enriched solution a metal salt, ammonia, an amine, a salt of ammonia or a salt of an amine.

Metal salts that may be used include hydroxides, alkoxides, halides, carbonates, borates, phosphates, thiocyanates, acetates, nitrates, sulfates, thiosulfates and any other salts that have a high solubility in water. The metals of the metal salts include lithium, sodium, potassium, calcium, magnesium, copper, iron, nickel, manganese, tin, zinc and aluminum. Preferred salts are salts of the following metal cations: $Li^+$, $Na^+$, $K^+$, $Ca^{2-}$, $Mg^{2+}$, $Cu^{2+}$, $Fe^{2+}$, $Fe^{3-}$, $Ni^{2+}$, $Mn^{2+}$, $Sn^{2+}$, $Zn^{2+}$ and $Al^{3+}$ of salts for inducing precipitation of a pravastatin metal salt are $Na^+$ and $K^+$.

Pravastatin may also be precipitated as an ammonium or amine salt by adding ammonia or an amine. The amine may be a primary, secondary or tertiary amine. Any alkyl or aryl amine that is not so hindered as to prevent ionic interaction between the amine nitrogen and the carboxyl group of pravastatin may be used. The amines include, but are not limited to, methyl, dimethyl, trimethyl, ethyl, diethyl, triethyl and other $C_1$–$C_6$ primary, secondary and tertiary amines; and further include morpholine, N-methylmorpholine, isopropyl cyclohexyl amine, piperidine and the like. Regardless of the absence, presence or multiplicity of substitution on nitrogen, a salt formed by reaction of ammonia or an amine is hereafter referred to as an ammonium salt. Its meaning is intended to encompass salts of amines as well as a salt of ammonia.

Precipitation of the ammonium salt of pravastatin may also be induced by addition of an ammonium salt either alone or in combination with ammonia, an amine or a metal salt. The preferred ammonium salts are the following salts of ammonia: $NH_4Cl$, $NH_4Br$, $NH_4I$, $(NH_4)_2SO_4$, $NH_4NO_3$, $(NH_4)_3PO_4$, $(NH_4)_2S_2O_4$, $NH^4OAc$ and $NH_4SCN$, the most preferred being $NH_4Cl$.

Metal salts, ammonium salts and high boiling liquid and solid amines may be added by conventional means, preferably in an area with good ventilation, either as solids, neat liquids or solutions in aqueous or organic solvent. Addition of gaseous ammonia requires special equipment for handling caustic gases. Such equipment, including pressure vessels, regulators, valves and lines are widely available. The ammonia may be introduced into the headspace above the enriched solution at ambient pressure or if a pressure vessel is used, at elevated pressure. Alternatively, the ammonia may be bubbled through the solution, which is preferably stirred to reduce clogging of the inlet tube by precipitated pravastatin ammonium salt.

In a preferred embodiment of the inventive process, pravastatin is obtained from the enriched solution as an ammonium salt by addition of ammonia or an amine. In a more preferred embodiment, pravastatin is obtained from the enriched solution as the pravastatin salt of ammonia by addition of gaseous ammonia to the enriched solution. Ammonia yields a highly polar ammonium salt of pravastatin which is easily precipitated in high yield from antisolvent. In the most preferred embodiment, pravastatin is obtained as the pravastatin salt of ammonia by addition of gaseous ammonia and an ammonium salt. The most preferred ammonium salt is $NH_4Cl$, which has the advantage of forming a concentrated aqueous ammonium chloride solution in the case of incomplete drying of the enriched organic solution.

The temperature at which the metal salt, ammonia, amine and/or ammonium salt should be added can be determined by routine experimentation by conducting the reaction on a small scale and monitoring the exothermicity of the reaction. Preferably, the solution temperature is not allowed to exceed 40° C. Although temperatures as high as 80° C. may be experienced without significant decomposition of pravastatin, many organic solvents of this invention will boil at a lower temperature. When ammonia is used, the preferred temperature range is from about –10° C. to about 40° C.

Once precipitation appears to cease or once consumption of pravastatin is determined to be substantially complete by other means, the addition should be ceased. When ammonia or a volatile amine is used, the vessel should be vented to disperse excess fumes. The crystals are then isolated by filtration, decantation of the solvent, evaporation of the solvent or other such method, preferably filtration.

After optionally washing the precipitated crystals, the pravastatin salt is purified by one or more recrystallizations. To purify the pravastatin salt, the salt is first dissolved in water. Preferably a minimum amount of water is used. Dissolution will generally require more water if an amine salt, instead of metal salt or salt of ammonia has been obtained. Once the pravastatin salt has completely dissolved, the polarity of the solution is decreased by addition of an anti-solvent. The anti-solvent is a water-soluble organic solvent or solvent mixture in which the pravastatin salt is poorly soluble. Suitable water-soluble organic solvents include acetone, acetonitrile, alkyl acetates, i-butanol and ethanol.

The pravastatin salt may be allowed to recrystallize spontaneously, or may be induced to recrystallize by taking further steps such as adding a common ion, cooling or adding a seed crystal. To further induce recrystallization by adding a common ion, a salt having the same metal or ammonium ion as the pravastatin salt is added to the mixture. Suitable salts for inducing recrystallization of the pravastatin salts are the same metal and ammonium salts as may be used to precipitate the pravastatin salt from the enriched solution. According to the preferred process wherein pravastatin is obtained as an ammonium salt, the chloride salt of ammonia or the amine previously used to obtain the pravastatin salt is added to induce recrystallization of the pravastatin salt. In the most preferred embodiment wherein the pravastatin salt of ammonia is obtained the added salt is most preferably $NH_4Cl$.

The recrystallization may be performed at between about –10° C. and about 60° C., preferably between about 0° C.

and about 50° C. and most preferably between about 0° C. and about 40° C. After the pravastatin salt has been substantially recrystallized from the solution, the crystals are isolated and may be washed, for example with a 1:1 mixture of i-butyl acetate and acetone and then dried. Drying may be conducted at ambient temperature but is preferably conducted at mildly elevated temperature of less than 45° C. and preferably about 40° C. The recrystallization may optionally be repeated to good effect as shown in Examples 7 and 8. Each repetition occurs in about 92–96% yield.

Even after recrystallization, the pravastatin contains an organic impurity which has a relative retention time (RRT) of 0.9 on HPLC. The organic impurity is estimated to be about 0.2% of the total composition based upon the HPLC chromatogram obtained with UV detection. The organic impurity can be removed as follows.

The pravastatin salt is dissolved in water, preferably a minimum or about 6 ml g$^{-1}$ and about 0.2% (v/v) isobutanol is then added. The pH is raised to from about pH 8 to about pH 14, preferably about pH 10 to about pH 13.7 by addition of sodium hydroxide and the mixture is maintained at a temperature of about 10° C. to about 50° C. for 10–200 minutes, preferably at a temperature of about 20° C. to about 30° C. for 60–100 minutes. The solution is then reacidified with a mineral or organic acid, preferably, hydrochloric acid or sulfuric acid to a pH of about pH 4 to about pH 9, more preferably about pH 5 to about pH 9 most preferably about pH 6 to about pH 7.5. After adjusting the pH, ammonium chloride is then added to the solution to salt out the pravastatin salt. If the amount of water used is about 6 ml g$^{-1}$, then use of about 2.0–2.3 g of ammonium chloride per gram of pravastatin salt is recommended. Preferrably the ammonium chloride is added portionwise over four to six hours.

After adding ammonium chloride, the pravastatin ammonium salt may crystallize spontaneously. Otherwise, recrystallization may be induced by cooling, seeding or other conventional means. While recrystallization is preferably induced via addition of a common ion, for example by adding ammonium chloride, recrystallization also may be induced by dilution with an anti-solvent as is preferably done in the recrystallization step previously described. However, in this operation care must be taken not to inadvertently precipitate pravastatin salts. As shown in more detail in Example 1, the amount of organic impurity with an RRT=0.9 was reduced beyond detectable limit and pravastatin ammonium was obtained in about 99.3% purity, approaching the level of purity that is acceptable for pharmaceutical use. At this stage of the inventive process, a pravastatin ammonia salt may be obtained with less than about 0.7% (w/w) organic impurities.

After removal of the organic impurities by recrystallization, the pravastatin salt is trans-salified to pravastatin sodium. Trans-salifying as it is used herein, refers to any process whereby the cation of an organic salt molecule is exchanged with another cation. In the trans-salification, pravastatin is first liberated from its metal or ammonium salt by dissolving the salt in an aqueous solvent, adding any protic acid such as hydrochloric, sulfuric, phosphoric trifluoroacetic or acetic acid to the aqueous solution and extracting pravastatin from the aqueous solution with an organic solvent. The protic acid is added to the aqueous solution in an amount that neutralizes or acidifies it, preferably acidifies it to a pH of about 1 to about 6, more preferably about 2 to about 4. Either before or after adding the protic acid to the aqueous solution, the aqueous solution is contacted with a water-immiscible organic solvent such as i-butyl acetate or any other water-immiscible organic solvent. After the aqueous solution has been contacted with a water-immiscible organic solvent and treated with the protic acid, the resulting organic phase containing pravastatin is then separated from the aqueous phase and, after optionally washing with water to remove ammonium residues, the pravastatin is back-extracted with aqueous sodium hydroxide. It is preferable to use an amount of NaOH that is only a modest molar excess over the amount pravastatin, preferably less than 1.1 equivalents thereof, more preferably less than 1.02 equivalents thereof.

After extraction into aqueous sodium hydroxide, excess sodium cations are scavenged to attain a near 1:1 equivalence of sodium cation and pravastatin. Scavenging is accomplished using water insoluble ionic exchange resins. Suitable ion exchange resins are the cationic and chelate type resins, the preferred being strong and weak acid exchange resins.

Among the strong acid cationic exchange resins which may be used are those having sulfonic acid ($SO_3^-H^+$) groups. These include the commercial products Amberlite® IR-118, IR-120, 252H; Amberlyst® 15, 36; Amberjet® 1200(H) (Rohm and Haas) Dowex® 50WX series, Dowex® HCR-W2, Dowex® 650C, Dowex® Marathon C, Dowex® DR-2030, and Dowex® HCR-S, ion exchange resins (Dow Chemical Co.); Diaion® SK 102 to 116 resin series (Mitsubishi Chemical Corp.) and Lewatit SP 120 (Bayer). The preferred strong acid cationic exchange resins are Amberlite® 120, Dowex® 50WX and Diaion® SK series.

Weak acid cationic exchange resins include those which have pendant carboxylic acid groups. Weak acid cationic exchange resins include the commercial products Amberlite® CG-50, IRP-64, IRC 50 and C67, Dowex® CCR series, Lewatit® CNP series and Diaion® WK series, of these, the most preferred are Amberlite® IRC50, Lewatit® CNP 80 and Diaion® WK 10. Less preferred are the chelate type exchange resins. Some of the commercial varieties that are available include Duolite® C-718, and C-467 (Rohm & Haas).

The solution containing pravastatin sodium salt and excess sodium cations may be contacted with the ion exchange resin by any method known to the art, including passage of the solution through a column or bed of the resin or by stirring a sufficient quantity of the resin in a flask with the solution. The mode of contact is not critical. After scavenging of the excess sodium ion, the pH of a pravastatin sodium solution should be in the range of about of 6.5 to about 10, preferably about 7.4 to about 7.8, although the pH will vary with dilution. Reduction in the pH of the pravastatin sodium solution from a higher pH to a lower pH and then leveling off of the pH at the lower level is an indication of substantial completion of scavenging excess $Na^+$ ions. After scavenging is complete, the pravastatin sodium solution is separated from the resin in a conventional manner. It may either be collected as the eluent from a column or bed or may be separated by filtration, decantation and the like.

Pravastatin sodium may be isolated from the pravastatin sodium solution by crystallization. Efficient crystallization may first require partial removal of the water, which can be conducted by vacuum distillation or nano-filtration. Preferably, the aqueous pravastatin sodium salt solution is concentrated from about 20 to about 50 w/v % before crystallizing. If necessary, after concentration the aqueous pravastatin sodium solution can be adjusted to a pH of between about 7 and about 10 with an ion exchange resin in $H^+$ form.

Addition of a water soluble organic solvent or organic solvent mixture to the pravastatin sodium solution will assist the crystallization. In particular, there may be mentioned acetone and acetone/acetonitrile, ethanol/acetonitrile and ethanol/ethyl acetate mixtures. One of the most preferred solvent system for crystallizing pravastatin sodium is a 1/3/12 water/acetone/acetonitrile mixture formed by concentrating the pravastatin sodium solution to about 30 w/v % and then adding an appropriate volume of 1/4 acetone/acetonitrile mixture. The other most preferred crystallization solvent mixture is water-acetone (1:15).

Pravastatin sodium also may be isolated by lyophilization of the aqueous pravastatin sodium solution.

Whether isolated by crystallization or other means that improves the purity of the product, the pravastatin sodium that is isolated in the practice of the present inventive process is substantially free of pravastatin lactone. As demonstrated in the examples that follow, pravastatin sodium may be isolated with less than 0.5% (w/w) total impurity content. Further, pravastatin sodium may be isolated with 0.2% (w/w) or less total impurity content by adhering to the preferred embodiments of the invention, two of which are exemplified in Examples 1 and 15. Major impurities which are part of the total impurity content include epipravastatin sodium, 3'-OH compactin sodium, 6-hydroxy isocompactin sodium and pravastatin lactone.

Although, the following examples illustrate the practice of the present invention in some of its embodiments. The examples should not be construed as limiting the scope of the invention. Other embodiments will be apparent to one skilled in the art from consideration of the specification and examples. It is intended that the specification, including the examples, is considered exemplary only, with the scope and spirit of the invention being indicated by the claims which follow.

EXAMPLES

Example 1
Purification of Pravastatin

The fermentation broth (100 L) was acidified to a pH from about 2.5 to about 5.0 by addition of sulfuric acid. The acidified fermentation broth was extracted with i-butyl acetate (3×50 L). The yield of i-butyl acetate extraction was found to be 95% by HPLC analysis calibrated to the internal standard in the broth. HPLC Conditions (Reverse phase): column: $C_{18}$, particle size 5 $\mu$m, length 150 mm, diameter 4.6 mm; mobile phase: 45% methanol/water, 0.1% $Et_3N$, 0.1% glacial acetic acid; flow rate 1.3 ml min.$^{-1}$; column temperature 25° C.; injection volume 10 $\mu$l; internal standard ethyl parahydroxybenzoate; detection: UV $\lambda$=238 nm.

The combined i-butyl acetate phases were then extracted with water (35 L) at about pH 7.5 to about pH 11.0 by addition of concentrated ammonium hydroxide. The resulting aqueous pravastatin solution was then reacidified to a pH of about 2.0 to about 4.0 by addition of 5M sulfuric acid and back-extracted with i-butyl acetate (8 L). The resulting solution of pravastatin in i-butyl acetate was partially dried over Perlite and $Na_2SO_4$. The pravastatin solution was decanted and then filtered from the drying agents and decolorized over activated charcoal (1.7 g). The solution was then filtered to remove the charcoal and transferred to a flask equipped with a gas inlet.

Ammonia gas was then introduced into the headspace above the solution at 15–25° C. with rapid stirring. After further precipitation appeared to cease, the ammonia was turned off and ammonium chloride was added to the mixture to ease filtration. The precipitated crystals of ammonium pravastatin carboxylate salt were collected by filtration and washed with i-butyl acetate and then acetone which yielded pravastatin ammonium salt in about 94% purity as determined by HPLC with UV detection at $\lambda$=238nm.

The pravastatin ammonium salt was further purified by crystallization from a saturated ammonium chloride solution as follows. The pravastatin salt containing 162 g of active substance was dissolved in water (960 ml) and diluted with acetone (96 ml) and i-butyl acetate (96 ml) at about 35–40° C. The solution was cooled to about 30–32° C. and pravastatin ammonium was induced to crystallize by addition of solid $NH_4Cl$ until further addition resulted in no apparent increase in crystal formation. After adding ammonium chloride, the solution was cooled to about 0–26° C. The pravastatin ammonium crystals were collected by filtration and washed with i-butyl acetate and acetone, as before, and then dried at about 40° C. The resulting pravastatin ammonium salt crystals (155.5 g) were obtained in about 98% purity as determined by HPLC employing the aforementioned conditions.

The pravastatin ammonium salt was further purified by another crystallization as follows. The pravastatin ammonium salt (155.5 g of active substance) was dissolved in water (900 ml). Isobutanol (2 ml) was added and then the pH was raised to about pH 10 to about pH 13.7 by addition of a concentrated solution of sodium hydroxide and the solution was stirred for 75 min. at ambient temperature. The solution was neutralized to a pH of about 7 by addition of sulfuric acid and crystallization of pravastatin ammonium was induced by addition of solid $NH_4Cl$. The crystals (150 g) were collected by filtration and washed with acetone. Pravastatin ammonium was found to be about 99.3% pure by HPLC detection using the above-described conditions.

The pravastatin ammonium was then trans-salified to the sodium salt as follows. The pravastatin ammonium salt crystals were dissolved in water (1800 ml). i-Butyl acetate (10.5 L) was added. The solution was then acidified to a pH of between from about pH 2 to about pH 4, by addition of sulfuric acid, which converted pravastatin back to its free acid. The i-butyl acetate phase, containing pravastatin, was washed with water (5×300ml). Pravastatin was then converted to its sodium salt and back-extracted into another aqueous phase by swirling the i-butyl acetate solution over water (900–2700 ml) with intermittent addition of 8m NaOH until a pH of between about pH 7.4 to about pH 13 was reached.

The pravastatin sodium salt solution was then treated with an ion exchange resin to scavenge excess sodium cations. After separation, the aqueous phase was stirred over Amberlite® IRC 50 exchange resin in the $H^+$ form for 30 min. at ambient temperature. Stirring was continued until a pH of about pH 7.4 to about pH 7.8 was reached.

The solution was then filtered to remove the resin and partially concentrated to a weight of 508 g. under vacuum. The solution was then diluted with acetonitrile (480 ml), giving a solvent 1.4:1 acetonitrile:water solvent mixture. The solution was stirred over activated carbon (5 g) to decolorize. After filtering of the activated carbon, pravastatin sodium was obtained as crystals by crystallization in 90% yield after further addition of acetone and acetonitrile to form a 1/3/12 mixture of water/acetone/acetonitrile (5.9 L) with cooling to about −10 to about 0° C. Pravastatin sodium was obtained in an overall yield of 65% in about 99.3% purity from the starting fermented active substance as measured by HPLC using the above-described conditions.

Example 2

Following the procedure in Example 1, but omitting the recrystallization from the water/acetone/acetonitrile mixture, pravastatin sodium was obtained by lyophilization of the concentrated solution of pravastatin sodium in water in about 99% purity and about 72% yield. Comparison of the ultimate purity of this example with Example 1 demonstrates that recrystallization of pravastatin sodium rather than lyophilization yields a somewhat purer product.

Examples 3–6

Following the procedure in Example 1, pravastatin sodium was isolated from a fermentation broth in the yield and purity shown in Table 1, when the corresponding organic solvent was used in the trans-salification process.

TABLE 1

| Example No. | Organic Solvent | Yield (%) | Purity (%) |
| --- | --- | --- | --- |
| 3 | $CH_2Cl_2$ | 63 | 96.6 |
| 4 | ethyl acetate | 58 | 99.5 |
| 5 | ethyl formate | 51 | 99.6 |
| 6 | butyl methyl ketone | 61 | 99.5 |

Example 7

Following the procedure of Example 1, but further purifying the pravastatin ammonium salt by once repeating the crystallization of the pravastatin ammonium salt, pravastatin sodium was obtained in about 99.6% purity and 58.4% yield.

EXAMPLE 8

Following the procedure of Example 1, but further purifying the pravastatin ammonium salt by twice repeating the crystallization of the pravastatin ammonium salt, pravastatin sodium was obtained in about 99.8% purity and 53% yield.

Example 9

Following the procedure of Example 1, the fermentation broth (100 L) was acidified to pH from about 2.5 to about 5.0. by addition of sulfuric acid. The acidified fermentation broth was extracted with i-butyl acetate (3×50 L). The combined i-butyl acetate phases were then extracted with water (35 L) having been basified to a pH of about pH 7.5 to about pH 11.0 by addition of concentrated ammonium hydroxide.

Instead of reacidifying the aqueous extract and extracting with i-butyl acetate to obtain a further enriched organic solution as was done in Example 1, the aqueous extract was concentrated to 140 g/L under vacuum. The resulting concentrated solution had a pH of about pH 4.0 to about pH 8. Excess ammonia was removed by evaporation.

Ammonium chloride crystals (405 g.) were then slowly added to the concentrated solution portionwise over four hours and the pravastatin ammonium salt was allowed to crystallize at ambient temperature. The crystals were then isolated by filtration and washed with a saturated solution of ammonium chloride. The crystals were then added to water (1L) at 40° C. After dissolution, the temperature was reduced to 30° C. and ammonium chloride (330 g.) was added to the solution portionwise over two hours. The solution was then stirred for 15 h at ambient temperature and crystals of pravastatin ammonium salt were recovered by filtration and washed with i-butyl acetate and after that with acetone and dried. The resulting crystals were then further purified by recrystallization transposed to the sodium salt and isolated as described in Example 1. Pravastatin sodium was obtained in about 99.6% purity and 64.7% yield.

Example 10

Following the procedure of Example 1, but the pravastatin sodium salt was crystallized from 1/15 mixture of water/acetone in an overall yield from the starting fermented active substance of 64% and in 99.6% purity as measured by HPLC.

Example 11

Following the method of Example 9, first two paragraphs, a concentrated aqueous extract (140 g. $L^{-1}$) was obtained. The concentrated aqueous extract was divided into three equal parts. The resulting concentrated solution was then acidified to a pH of about pH 4.0 to about pH 8.0 by addition of 1M HCl. Following the method of Example 9, third paragraph, but substituting the salts in Table 2 for ammonium chloride, a pravastatin salt was precipitated from each of the portions and transposed to the sodium salt.

TABLE 2

| Salts | Purity (%) | Yield (%) |
| --- | --- | --- |
| KCl | 99.3 | 42 |
| NaCl | 99.4 | 38 |
| LiCl | 99.1 | 34 |

We claim:

1. A process for isolating a sodium salt of a compound selected from the group consisting of pravastatin, compactin and lovastatin, from a fermentation broth comprising the steps of:
   a. forming an enriched solution of the compound;
   b. obtaining a salt of the compound from the enriched solution;
   c. purifying the salt of the compound;
   d. trans-salifying the salt of the compound to a sodium salt of the compound by:
      i. liberating the compound from its salt,
      ii. contacting the compound with an aqueous sodium hydroxide solution thereby forming an aqueous solution of the sodium salt of the compound, and
      iii. scavenging excess sodium ions by contacting the aqueous solution of the sodium salt of the compound with a water-insoluble ionic exchange resin; and
   e. isolating the sodium salt of the compound from the aqueous solution of the sodium salt of the compound.

2. The process of claim 1 wherein the enriched solution is an enriched aqueous solution that is formed by the steps of:
   a) contacting an acidic fermentation broth with an organic extraction solvent and thereby forming an organic extract of the compound;
   b) back-extracting the organic extract by contacting with a basic aqueous solution thereby forming an aqueous extract; and
   c) concentrating the aqueous extract thereby forming an enriched aqueous solution of the compound.

3. The process of claim 1 wherein the enriched solution is an enriched organic solution that is formed by the steps of:
   a) contacting an acidic fermentation broth with an organic extraction solvent and thereby forming an organic extract of the compound;
   b) back-extracting the organic extract by contacting with a basic aqueous solution thereby forming an aqueous extract of the compound; and
   c) re-extracting the compound from the aqueous extract by contacting with an organic re-extraction solvent thereby forming an enriched organic solution of the compound.

4. The process of claim 2 wherein concentrating the aqueous extract is carried out by vacuum distillation.

5. The process of claim 2 wherein contacting the acidic fermentation broth with the organic extraction solvent is carried out at a pH of between about pH 1 and about pH 6.

6. The process of claim 2 wherein back-extracting with a basic aqueous solution is carried out at a pH of between about pH 7.0 and about pH 13.7.

7. The process of claim 2 wherein the organic extraction solvent is selected from the group consisting of $C_2$–$C_4$ alkyl formates, $C_1$–$C_4$ alkyl esters of $C_2$–$C_4$ alkyl carboxylic acids, dichloromethane, dichloroethane, chloroform, carbon tetrachloride and butyl methyl ketone.

8. The process of claim 7 wherein the organic extraction solvent is an acetate.

9. The process of claim 3 wherein contacting the acidic fermentation broth with an organic extraction solvent is carried out at a pH of between about pH 1 and about pH 6.

10. The process of claim 3 wherein back-extracting with a basic aqueous solution is carried out at a pH of between about pH 7.0 and about pH 13.7.

11. The process of claim 3 wherein re-extracting the compound with an organic solvent is carried out at a pH of between about pH 1 and about pH 6.

12. The process of claim 3 wherein the organic extraction solvent and the organic re-extraction solvent are each independently selected from the group consisting of $C_2$–$C_4$ alkyl formates, $C^1$–$C_4$ alkyl esters of $C_2$–$C_4$ alkyl carboxylic acids, dichloromethane, dichloroethane, chloroform, carbon tetrachloride, butyl methyl ketone.

13. The process of claim 12 wherein the organic extraction solvent and organic re-extraction solvent are acetates.

14. The process of claim 13 wherein the organic extraction solvent and organic re-extraction solvent are i-butyl acetate.

15. The process of claim 1 wherein obtaining of the salt of the compound is carried out at temperature of between about $-10°$ C. and about $+60°$ C.

16. The process of claim 1 wherein obtaining of the salt of the compound comprises precipitating the salt of the compound by adding a metal salt, ammonia, an amine or an ammonium salt to the enriched solution.

17. The process of claim 16 wherein the salt of the compound is precipitated by adding an ammonium salt.

18. The process of claim 17 wherein the ammonium salt is selected from the group consisting of $NH_4Cl$, $NH_4Br$, $NH_4I$, $(NH_4)_2SO_4$, $NH_4NO_3$, $(NH_4)_3PO_4$, $(NH_4)_2S_2O_4$, $NH_4OAc$ and $NH_4SCN$.

19. The process of claim 18 wherein the ammonium salt is $NH_4Cl$.

20. The process of claim 16 wherein the salt of the compound is precipitated by adding ammonia gas.

21. The process of claim 16 wherein the salt of the compound is precipitated by adding ammonia gas and an ammonium salt.

22. The process of claim 16 wherein the salt of the compound is precipitated by adding a metal salt.

23. The process of claim 22 wherein the metal salt is selected from the group consisting of lithium salts, sodium salts, potassium salts, calcium salts, magnesium salts, copper salts, iron salts, nickel salts, manganese salts, tin salts, zinc salts and aluminum salts.

24. The process of claim 23 wherein the metal salt is selected from the salts containing the metal ions $Li^+$, $Na^+$, $K^+$, $Ca^{2+}$, $Mg^{2+}$, $Cu^{2+}$, $Fe^{2+}$, $Fe^{3-}$, $Ni^{2+}$, $Mn^{2+}$, $Sn^{2+}$, $Zn^{2+}$, $Al^{3+}$ ions.

25. The process of claim 16 wherein the salt of the compound is precipitated by adding an amine salt.

26. The process of claim 25 wherein the amine salt has an amine component selected from the group consisting of $C_1$–$C_3$ primary, secondary and tertiary alkyl amines.

27. The process of claim 1 wherein the step of purifying the salt of the compound comprises the step of recrystallizing the salt of the compound.

28. The process of claim 27 wherein recrystallizing the salt of the compound comprises the steps of:
a) dissolving the salt of the compound in water thereby forming an aqueous solution of the salt of the compound;
b) diluting the aqueous solution of the salt of the compound with an anti-solvent; and
c) adding a salt having the same metal, ammonium or aminium ion as the salt of the compound.

29. The process of claim 28 wherein the anti-solvent is selected from the group consisting of ethyl acetate, i-butyl acetate, i-butanol, acetone, acetonitrile and ethanol.

30. The process of claim 28 wherein the salt having the same metal, ammonium ion or aminium ion as the salt of the compound is an ammonium salt.

31. The process of claim 30 wherein the ammonium salt is selected from the group consisting of $NH_4Cl$, $NH_4Br$, $NH_4I$, $(NH_4)_2SO_4$, $NH_4NO_3$, $(NH_4)_3PO_4$, $(NH_4)_2S_2O_4$, $Nh_4OAc$ and $NH_4SCN$.

32. The process of claim 31 wherein the ammonium salt is $NH_4Cl$.

33. The process of claim 1 wherein liberating the compound from the salt of the compound comprises the steps of:
a) dissolving the salt of the compound in aqueous solvent,
b) adding a protic acid to the aqueous solvent, and
c) extracting the compound from the aqueous solvent into an organic solvent to form an organic solution of the compound, further wherein the compound is contacted with the aqueous sodium hydroxide solution by back-extracting the organic solution of the compound with the aqueous sodium hydroxide solution.

34. The process of claim 33 wherein extracting the compound is carried out at a pH between about pH 1 and about pH 6.

35. The process of claim 33 wherein the organic solvent is selected from the group consisting of $C_2$–$C_4$ alkyl formates, $C_1$–$C_4$ alkyl $C_2$–$C_4$ alkanoates, dichloromethane, dichloroethane, chloroform, carbon tetrachloride and butyl methyl ketone.

36. The process of claim 35 wherein the organic solvent is i-butyl acetate.

37. The process of claim 33 wherein the back-extracting of the organic solution of the compound into an aqueous solution of sodium hydroxide is carried out at a pH of between about pH 6.5 and about pH 13.7.

38. The process of claim 1 wherein isolating the sodium salt of the compound comprises the steps of:
a) concentrating the aqueous solution of the sodium salt of the compound and
b) diluting the aqueous solution of the sodium salt of the compound with an organic solvent or organic solvent mixture.

39. The process of claim 1 wherein isolating the sodium salt of the compound comprises the step of lyophilizing the aqueous solution of the sodium salt of the compound.

40. The process of claim 38 wherein concentrating the aqueous solution of the sodium salt of the compound is carried out by vacuum distillation.

41. The process of claim 38 wherein concentrating the aqueous solution of the sodium salt of the compound is carried out by nano-filtration.

42. The process of claim 38 wherein the aqueous solution of the sodium salt of the compound is diluted with acetone.

43. The process of claim 38 wherein the aqueous solution of the sodium salt of the compound is diluted with an organic solvent mixture selected from the group consisting of acetone/acetonitrile mixtures, ethanol/acetonitrile mixtures and ethanol/ethyl acetate mixtures.

44. The process of claim 38 wherein isolating the sodium salt of the compound is carried out at a temperature of between about $-10°$ C. and about $+60°$ C.

* * * * *